US00PP16517P3

(12) United States Plant Patent
Danziger

(10) Patent No.: US PP16,517 P3
(45) Date of Patent: May 9, 2006

(54) ***LIMONIUM* PLANT NAMED 'DANLISABLUE'**

(50) Latin Name: *Limonium altaica*
Varietal Denomination: Danlisablue

(75) Inventor: Gabriel Danziger, Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 86 days.

(21) Appl. No.: 10/829,354

(22) Filed: Apr. 22, 2004

(65) Prior Publication Data

US 2005/0241040 P1 Oct. 27, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Foley & Lardner, LLP

(57) ABSTRACT

A new and distinct *Limonium* plant named 'Danlisablue' particularly characterized by the combination of violet-blue flower color, RHS 93 B; high stems measuring 70–90 cm; panicle branching habit; flexible stems; and a yield of 6–10 stems per plant in the first flash.

2 Drawing Sheets

Latin name of the genus and species of the claimed plant: *Limonium altaica.*
Variety denomination: 'Danlisablue'.

BACKGROUND OF THE INVENTION

The present invention relates to a new and distinct cultivar of *Limonium* plant, botanically known as *Limonium altaica,* hereinafter referred to by the variety denomination 'Danlisablue'.

*Limonium* of the Plumbaginaceae family, is commonly known as sealavender. *Limonium* is found wild on sea coasts and marshes across the Northern Hemisphere.

The new cultivar originated from an open pollination of *Limonium* plants within a breeding program field, discovered in a controlled environment in Moshav Mishmar Hashiva, Israel. The female parent is proprietary cultivar designated 'PTE' (unpatented). The male parent is unknown. 'Danlisablue' was discovered and selected by the inventor, Gabriel Danziger, as a flowering plant within the progeny of the open pollination program in Moshav Mishmar Hashiva, Israel.

Asexual reproduction of the new cultivar by tissue culture was first performed in August, 2001, in Moshav Mishmar Hashiva, Israel, and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be basic characteristics of 'Danlisablue' which in combination distinguish this *Limonium* as a new and distinct cultivar:

1. violet-blue flower color, RHS 93 B;
2. high stems measuring 70–90 cm;

3. panicle branching habit;
4. flexible stems; and
5. yield of 6 to 10 stems per plant in the first flash.

'Danlisablue' has not been observed under all possible environmental conditions. The phenotype of the new cultivar may vary with variations in environment such as temperature, light intensity, and daylength without any change in the genotype of the plant. The following observations, measurements and values describe the new cultivar as grown in Moshav Mishmar Hashiva, Israel under conditions which closely approximate those generally used in commercial practice.

Table 1 provides a comparison between plants of 'Danlisablue' and plants of the parent, 'PTE' (unpatented).

TABLE 1

| Trait | 'Danlisablue' | Female Parent 'PTE' (unpatented) |
|---|---|---|
| Flower color | Violet-blue group, RHS 93B | Violet-blue group, RHS 93D |
| Number of Flowers | Approximately 30 flowers in full bloom | Approximately 30 flowers in full bloom |
| Growth and Branching Habit | Erect growth habit; panicle branching habit | Erect growth habit; panicle branching habit |
| Yield of Stems | 6–10 stems per plant in the first flash | 8–12 stems per plant in the first flash |

Of the many commercial cultivars known to the inventor, the most similar in comparison to 'Danlisablue' is the cultivar 'Tall Emille' (unpatented). In comparison to 'Tall Emille', 'Danlisablue' has flexible stems whereas 'Tall Emille' has durable stems, and 'Danlisablue' has a narrow shaped inflorescence and panicle branching habit while 'Tall Emille' has an open and wide shaped inflorescence.

Type of Branching

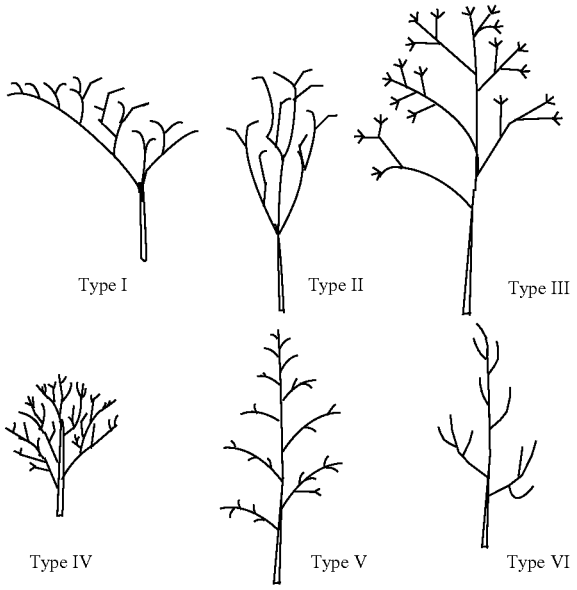

BRIEF DESCRIPTION OF THE DRAWINGS

The accompanying photographic drawings illustrate the overall appearance of the new *Limonium* showing the colors as true as is reasonably possible with color reproductions of this type. The first photograph shows a top view of a flowering 'Danlisablue' plant. The second photograph shows a side view of a flowering 'Danlisablue' plant.

DETAILED BOTANICAL DESCRIPTION

The following observations, measurements and values describe the new cultivar as grown in Moshav Mishmar Hashiva, Israel, in Mediterranean climate at sea level, under conditions which closely approximate those generally used in commercial practice. Irrigation and fertilization use is common to commercial practice for *Limonium*.

Color references are made to The Royal Horticultural Society Colour Chart (R.H.S) (published 2001) except where general colors of ordinary significance are used. Color values were taken under daylight conditions at approximately 10:00 AM in Moshav Mishmar Hashiva, Israel. The age of the plant described was 1 year old, in its second flash and the stem which used to determine the R.H.S colour was at 30–50% open flower stage.

Plant: General Appearance and Form:

*Height.*—70–90 cm.

*Spread.*—40–50 cm.

*Growth habit.*—Erect.

*Growth rate.*—7–9 weeks from planting to the first bloom.

*Branching habit and description.*—Panicle.

*Flowering stem length.*—70–90 cm.

*Flowering response.*—Day natural.

*Flowering season.*—All year; spring, summer and autumn in open field, during the winter in greenhouse.

*Winter hardiness/weather tolerance.*—Frost tender.

*Postproduction longevity.*—2 weeks.

*Time to initiate roots.*—Once tissue culture plantlets show small roots, plantlets are transferred from the tissue culture medium to a peat soil, then placed in 100% humid condition for 7–14 days at 18–35° C., then the plantlets are transferred to regular irrigation and fertilization.

*Time to produce a rooted cutting.*—30 to 45 days from the arrival from the tissue culture laboratory until the plants are ready to plant.

*Fragrance.*—None.

Stems:

*Appearance.*—Panicle.

*Aspect.*—Stable, Erect.

*Length.*—70–90 cm.

*Diameter.*—Typical: 1–2 mm. Observed: 1–2 mm.

*Texture.*—Smooth.

*Color.*—Green Group, RHS 139 A.

*Internode length.*—Typical: 7–10 cm. Observed: 7–10 cm.

Foliage:

*Overall shape of leaf.*—Obovate.

*Apex.*—Obtuse.

*Base.*—Cuneate.

*Length.*—15–30 cm.

*Width.*—4–6 cm.

*Margin.*—Entire.

*Texture.*—Smooth.

*Color of upper surface.*—Mature leaf: Green Group, RHS 136 A. Immature leaf: Green Group, RHS 136 A.

*Color of lower surface.*—Mature leaf: Green Group, RHS 136 B. Immature leaf: Green Group, RHS 136 B.

*Venation.*—None.

*Petiole.*—Length: 3–12 cm. Diameter: 3–4 mm. Color: Green Group, RHS 141 C.

Inflorescence:

*Flower type and habit.*—Erect, trumpet shaped.

*Flower size.*—Diameter: 0.5–0.8 mm. Depth: 0.5 mm.

*Overall shape.*—Trumpet shaped.

*Calyx.*—Shape: Tubular. Length: 0.5 mm. Width: 1 mm. Margin: Entire. Texture: Smooth. Color when opening: White, RHS 155A, at the base and violet-blue, RHS 93D, at the top. Color when fully open: White, RHS 155A, at the base and violet-blue, RHS 93D, at the top.

*Corolla.*—Shape: Round Saucer-shaped. Number of petals: 5 separate petals. Diameter: 5–7 mm. Depth: Typical: 0.7 cm. Observed: 0.7 cm.

*Petals.*—Length: 3 mm. Width: 1 mm. Overall shape: Oblong. Apex shape: Truncate. Base shape: Cuneate. Margin: Entire. Texture: Smooth. Color when opening: Upper surface: Violet-Blue Group RHS 93 B. Lower surface: Violet-Blue Group RHS 93 B. Color when fully open: Upper surface: Violet-Blue Group RHS 93 B. Lower surface: Violet-Blue Group RHS 93 C.

*Sepals.*—Quantity: 4. Shape: Oval when stretched out and semi tubular on the plant. Length: 2–4 mm. Width: 1–2 mm. Form: Alternate, very dense.

*Bud.*—Color: Violet-Blue, RHS 93 B. Shape: Oblong. Length: 2–3 mm. Diameter: 1 mm.

*Peduncle description.*—Borne from 2 sepals, 4 mm long, smooth texture; green color, RHS 141 C.

Reproductive organs:

*Stamen.*—5 in number; white in color.

*Anthers.*—5 in number, 0.5–1 mm in length; brown-black in color.

*Pistil.*—5 in number.

*Stigma.*—Filament, white in color.

*Style.*—Filament; white in color.

*Ovary.*—Green in color.

*Seeds.*—Width: 1 mm. Length: 2 mm. Shape: Oval. Color: Brown.

*Fruit.*—White-brown in color.

*Pollen.*—Yellow in color.

Disease/pest resistance/susceptibility: Unknown.

Weather tolerance: Plants of 'Danlisablue' have exhibited good tolerance to draught, rain and wind, however flowering may cease during hot periods (temperatures above 30° C.).

I claim:

1. A new and distinct *Limonium* plant named 'Danlisablue', as illustrated and described herein.

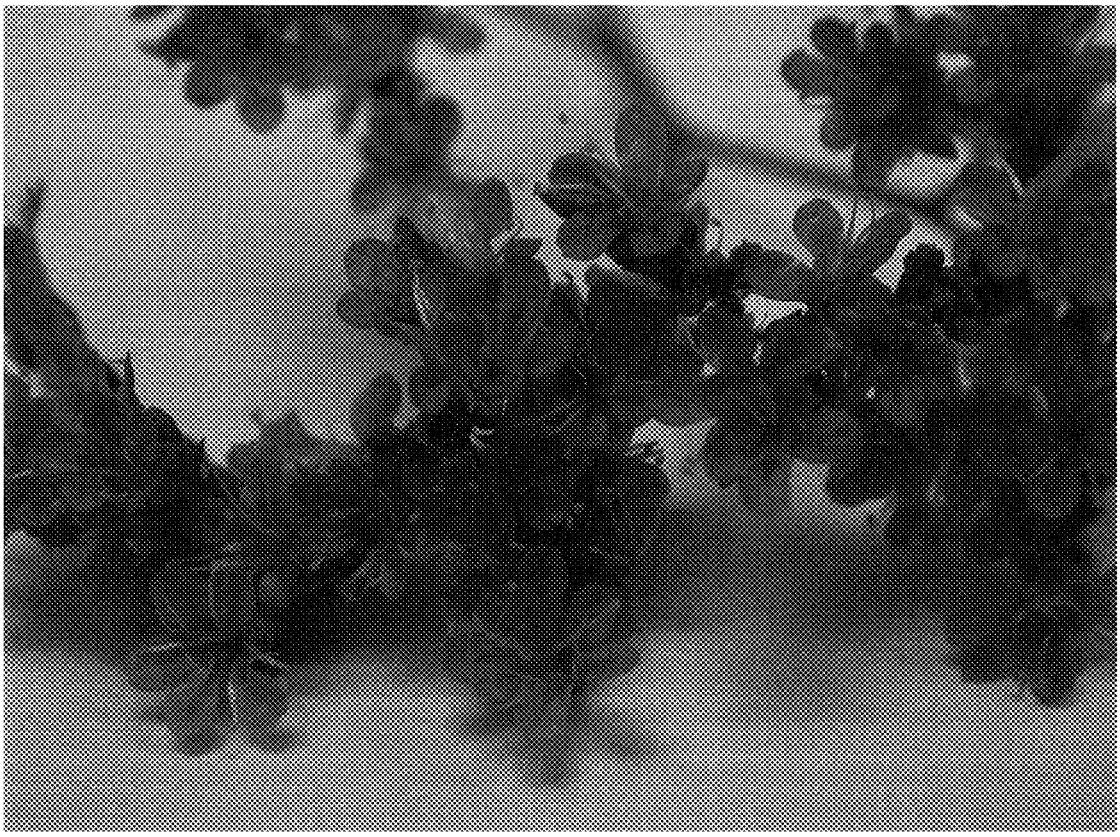

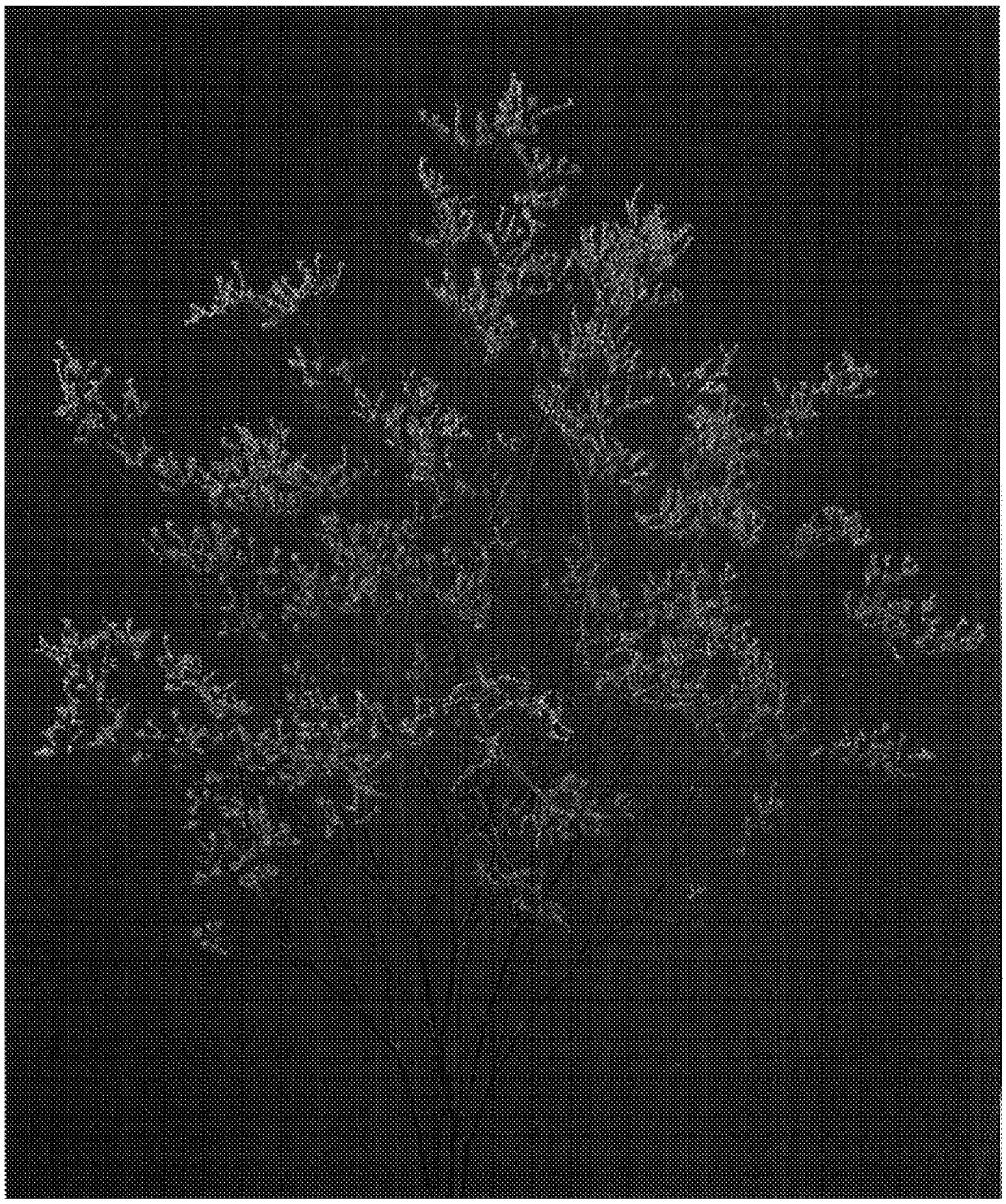

* * * * *